United States Patent
Briant et al.

(10) Patent No.: US 9,289,565 B2
(45) Date of Patent: *Mar. 22, 2016

(54) INHALER WITH INDEXING LINKED TO MOVEMENT OF COVER

(75) Inventors: John Briant, Hertfordshire (GB); Patrick Campbell, Hertfordshire (GB); Charles Cooke, Hertfordshire (GB); Christopher Groombridge, Hertfordshire (GB); James Daniel John, Hertfordshire (GB); Trevor John Penhallurick, Hertfordshire (GB); William Bakewell, Hertfordshire (GB); Nicholas Harrison, Cambridgeshire (GB)

(73) Assignee: ASTRAZENECA AB (SE)

( * ) Notice: Subject to any disclaimer, the term of this patent is extended or adjusted under 35 U.S.C. 154(b) by 1200 days.

This patent is subject to a terminal disclaimer.

(21) Appl. No.: 13/123,140

(22) PCT Filed: Oct. 7, 2009

(86) PCT No.: PCT/SE2009/051112
§ 371 (c)(1),
(2), (4) Date: Jul. 1, 2011

(87) PCT Pub. No.: WO2010/042035
PCT Pub. Date: Apr. 15, 2010

(65) Prior Publication Data
US 2011/0259326 A1    Oct. 27, 2011

Related U.S. Application Data

(60) Provisional application No. 61/103,599, filed on Oct. 8, 2008.

(51) Int. Cl.
*A61M 15/00* (2006.01)

(52) U.S. Cl.
CPC ....... *A61M 15/0091* (2013.01); *A61M 15/0003* (2014.02); *A61M 15/0026* (2014.02); *A61M15/0043* (2014.02); *A61M 15/0045* (2013.01); *A61M 15/0048* (2014.02); *A61M 2202/064* (2013.01); *A61M 2205/073* (2013.01)

(58) Field of Classification Search
CPC ................... A61M 2201/064; A61M 15/0065; A61M 15/00; A61M 15/009; A61M 16/12; A61M 16/104; A61M 16/18; A61M 15/0001–15/001; A61M 15/0013–15/0026; A61M 15/0028–15/0045; A61M 15/0056; A61M 15/006; A61M 15/0068–15/0085; A61M 15/0091–15/0098; A61M 2202/064; A61J 1/2006–1/2017; A61K 9/14
USPC ............. 128/203.12, 203.15, 203.19, 203.21, 128/200.11–200.24; 604/58; 222/168.5
See application file for complete search history.

(56) References Cited

U.S. PATENT DOCUMENTS 5,388,572 A * 2/1995 Mulhauser et al. ...... 128/203.15
5,492,112 A * 2/1996 Mecikalski et al. ..... 128/203.15
(Continued)

FOREIGN PATENT DOCUMENTS

EP     2082759        7/2009
JP     2005-523748 A  8/2005
(Continued)

OTHER PUBLICATIONS

International Search Report from Swedish Patent Office mailed on Jan. 22, 2010.

*Primary Examiner* — Jason Flick
*Assistant Examiner* — Ned T Heffner
(74) *Attorney, Agent, or Firm* — Finnegan, Henderson, Farabow, Garrett & Dunner, LLP

(57) ABSTRACT

The disclosure relates to a medical dispenser, comprising an outlet and a plurality of sealed compartments containing medicament to be sequentially aligned with and dispensed through said outlet. Movement of an actuator sequentially causes mechanical energy to be built up and then released and converted into an indexing movement of the compartments. The disclosure also relates to an indexing method for a medical dispenser.

15 Claims, 8 Drawing Sheets

(56) References Cited

U.S. PATENT DOCUMENTS

| | | | |
|---|---|---|---|
| 5,542,411 A * | 8/1996 | Rex .................... | 128/203.15 |
| 5,787,881 A * | 8/1998 | Chawla .................... | 128/203.15 |
| 6,880,555 B1 * | 4/2005 | Brunnberg et al. ...... | 128/203.12 |
| 2005/0087191 A1 | 4/2005 | Morton et al. | |
| 2005/0178382 A1 * | 8/2005 | Riley et al. ............... | 128/203.15 |
| 2008/0001008 A1 | 1/2008 | Thoemmes et al. | |

FOREIGN PATENT DOCUMENTS

| | | |
|---|---|---|
| JP | 2007/512856 A | 5/2007 |
| JP | 2007-533363 A | 11/2007 |
| WO | WO 96/28202 | 9/1996 |
| WO | WO 02/24263 | 3/2002 |
| WO | WO 02/24265 | 3/2002 |
| WO | WO 02/100470 A1 | 12/2002 |
| WO | WO 03/051839 A1 | 6/2003 |
| WO | WO 03/090811 A2 | 11/2003 |
| WO | WO 2005/002654 | 1/2005 |
| WO | WO 2005/037353 A1 | 4/2005 |
| WO | WO 2006/000758 A1 | 1/2006 |
| WO | WO 2006/071512 A1 | 7/2006 |
| WO | WO 2008/010765 A1 | 1/2008 |
| WO | WO 2009/008001 | 1/2009 |

* cited by examiner

INHALER WITH INDEXING LINKED TO MOVEMENT OF COVER

This is a U.S. National Phase Application of PCT/SE2009/051112, filed on Oct. 7, 2009, which claims the benefit of priority to U.S. Provisional Application No. 61/103,599, filed on Oct. 8, 2008, all of which are incorporated herein by reference.

TECHNICAL FIELD

The present invention relates to a medical dispenser comprising an outlet and a plurality of sealed compartments containing medicament to be sequentially aligned with and dispensed through said outlet. The invention also relates to an indexing method for a medical dispenser.

BACKGROUND OF THE INVENTION

There are various types of medical dispensers, such as packages or devices for dispensing tablets, salves or inhalable substances, to mention a few. Some dispensers are provided with one or more sealed compartments containing medicament. Such compartments may take the form of blisters, pockets or a cavities-containing strip joined to a sealing strip or other suitable forms.

Taking medical dispensers in the form of inhalers, there are different types available on the market. A pressurized Metered Dose Inhaler (pMDI) releases a fixed dose of substance in aerosol form. A powder inhaler generally releases a dose of powdered substance entrained in an air stream. In a powder inhaler the powder may be provided in a bulk container of the inhaler from which doses of powder are metered for dispensing. As an alternative to a bulk container, powder inhalers may comprise a single compartment or a plurality of compartments for containing one or more discrete doses of powdered substance.

Powder inhalers comprising a plurality of compartments containing discrete doses of powdered substance, generally comprise some kind of indexing mechanism for moving the compartments sequentially into position for inhalation and also some kind of opening mechanism for accessing the substance contained in the compartments. Although some inhalers allow a short backward indexing to occur, i.e. move the compartments in a direction opposite to the normal use direction, it may be undesirable in combination with certain types of opening mechanisms, e.g. due to risk of components interfering. The normal forward indexing in an inhaler may usually be triggered by some kind of actuator, such as a lever or an outlet cover, which, when moved, causes the compartments to move. If the actuator is moved only a part of the distance, there is a risk of "half indexing", i.e. the compartments do not move the intended distance in full. This in turn may lead to incorrect dose administration. Apart from being present in inhalers, these drawbacks of backward indexing and half-indexing could also be present in other types of medical dispensers. It would be desirable to provide a medical dispenser and an indexing method which can avoid backward indexing and/or half-indexing.

SUMMARY OF THE INVENTION

An object of the present invention is to avoid the drawbacks of the prior art medical dispensers. This and other objects, which will become apparent in the following, are accomplished by the inhaler and the method defined in the accompanied claims.

The present invention is based on the insight that an output caused by the movement of an actuator may be temporarily stored and utilized later. By choosing at what point in time the stored output should be made use of, a desired control is obtainable. Thus, rather than having the indexing movement being performed substantially simultaneously with (directly driven by) the movement of the actuator, the indexing movement may be postponed. For instance, the output of the actuator movement may be configured to be used only when the actuator has moved a certain distance, in particular the output may be used for an indexing movement. Thus, if a user only moves the actuator halfway and then back again, there will be no indexing, thereby making it possible to avoid backward and half-indexing problems. By postponing the use of the actuator output, it is possible to design an indexing mechanism having two possible modes: a non-indexing mode and a complete-indexing mode.

According to a first aspect of the invention, a medical dispenser is provided. The dispenser comprises
an outlet,
a plurality of sealed compartments containing medicament to be sequentially aligned with and dispensed through said outlet,
an actuator movable between a first position and a second position,
wherein movement of the actuator from the first position towards the second position causes mechanical energy to be built up, wherein the arrival of the actuator at the second position causes the built-up mechanical energy to be released and converted into an indexing movement of the compartments.

Thus, although the indexing movement is operatively connected to the movement of the actuator, rather than being a substantially parallel course of action, the indexing movement is delayed until the actuator has moved a certain distance. Although it would be possible to use the actuator only for priming the indexing mechanism, and then manually use a separate component for releasing the indexing mechanism, the present invention achieves the delay automatically, since the delay is controlled in relation to the position of the actuator. Said second position may be appropriately located along the length of travel of the actuator. For instance, by locating said second position at or near the end of the maximum allowable travel of the actuator, the indexing will only occur if the user completes or almost completes the full available movement of the actuator. This may be advantageous in several respects. For instance, if the movement of the actuator also affects a compartment opening mechanism, the sequence in which the various components move may be chosen by appropriate location of said second position.

The build up of mechanical energy may be designed to be a continuous increase or accumulation of energy. Thus, as long as the actuator is continued to move towards the second position the accumulation of energy is continued. However, the build up of mechanical energy could, as an alternative, be designed as an initial increase of energy during an initial part of the movement towards the second position of the actuator, and then said energy is just maintained without increase during the remaining part of the movement towards the second position.

According to at least one example embodiment of the invention, the medical dispenser comprises
an indexing mechanism for sequentially aligning the compartments with the outlet, wherein the indexing mechanism is operatively connected to the actuator, wherein said mechanical energy is built up in the indexing mechanism, and a counteracting member having a counteracting position, in which the counteracting member temporarily prevents said mechanical energy from being released, and a release position, in which the mechanical energy is released whereby the indexing mechanism is allowed to advance the compartments, wherein the counteracting member is operatively connected to the actuator such that the counteracting member reaches said release position when the actuator reaches said second position.

By providing said counteracting member with a release position which is associated with said second position of the actuator, a distinct and predictable release of the mechanical energy is obtainable. Although the disclosed counteracting member provides advantages, other alternatives for releasing the mechanical energy are conceivable. For instance, there may be provided a delay member which sets a force threshold to be overcome by the indexing mechanism. As the actuator reaches its second position, the indexing mechanism has accumulated enough energy to exert a force on the delay member which is larger than said threshold, whereby the delay member gives way for the indexing mechanism which is then allowed to index and place the next compartment aligned with the outlet.

In this application the expression "aligned with the outlet" should be understood as having provided the compartment in a position for administration of the contained medicament through the outlet. In the case of the medical dispenser being in the form of an inhaler, the expression "aligned with the outlet" should be understood as having the compartment in a position for inhalation of the contained medicament through the outlet, wherein the outlet may be a mouthpiece or a nasal adaptor.

The mechanical energy may be built up in various types of arrangements, such as arrangements comprising piezoelectric components or movable rigid components such as levers. According to at least one example embodiment, the indexing mechanism comprises a spring in which said mechanical energy is built up. The word spring should be understood in its broadest sense. Thus, it includes any elastic object for variously storing and furnishing energy. It may be made of any suitable elastic material, e.g. metal, such as steel alloys, or rubber or plastic, etc. Just to mention a few conceivable alternatives, the spring may be a torsion spring, coil spring, leaf spring, compression spring, extension spring, etc, but it may also be a piece of rubber which is compressed and then upon release of the stored energy affects another part of the indexing mechanism.

According to at least one example embodiment, said indexing mechanism comprises a drive member which is engagable with the compartments or a structure carrying the compartments, the drive member being connected to the spring so that when the counteracting member reaches said release position, the accumulated mechanical energy in the spring is transmitted via the drive member to the compartments. The spring may either become connected to the drive member at the time of release of the mechanical energy, or it may be in constant contact with the drive member. In the latter case, as the spring becomes energized, the drive member will be increasingly urged to move the compartments forward, however, the force of the counteracting member prevents such movement. Thus, the compartments or said structure carrying the compartments will become biased to move in the forward indexing direction. Although the use of a drive member has been discussed in detail above, an alternative would be to have the spring in direct contact with the compartments or the structure carrying the compartments, without the intermediate drive member.

According to at least one example embodiment, when the counteracting member is in said counteracting position, it is in a fixating contact with one or more compartments or with a structure carrying the compartments. Thus, the counteracting member directly prevents the compartments from becoming indexed. An alternative would be to have the counteracting member in fixating contact with either the drive member or the spring, thereby indirectly preventing the compartments from becoming indexed.

According to at least one example embodiment, the medical dispenser comprises a rotatable disk holding said compartments, wherein, in said counteracting position, the counteracting member engages the disk to prevent it from rotating. It should be understood that the counteracting member could also be applied on other movable structures that carry medicament, e.g. strips, blister packs etc. Likewise, although a circular disk provides advantages, a counteracting member may be applied onto any structure shape, e.g. rectangular, cylindrical etc.

According to at least one example embodiment, the medical dispenser comprises a track which moves with the actuator, wherein the counteracting member comprises a brake adapted to prevent the compartments from moving, and a follower which is connected to the brake and which travels along said track in response to the movement of the actuator, wherein when the follower reaches a point of release the connected brake is released. The track may be provided in various manners, e.g. on a movable wall structure or insert within the medical dispenser, wherein the actuator is connected to the movable wall structure or insert. The track may be in the form of an elongated groove in which a mating portion of the follower is received. Alternatively, the track may be an elongated rail on which a mating portion of the follower is placed.

Although the above-described embodiment comprises a track which cooperates with the counteracting member, the movement of the counteracting member from its counteracting position to its release position, may be achieved in other ways as well. For instance, when the actuator reaches the second position, it could engage with a lever or switch which acts upon the counteracting member to move it to the release position.

In order to reduce the risk of over-indexing, i.e. moving the compartment more than one compartment step (approximately the distance between neighbouring compartments) at a time, there may be provided means which limits the freedom of movement. This is reflected in at least one example embodiment, according to which a stop element which, during said indexing movement, is adapted to engage with the compartments or a structure carrying the compartments in order to limit said movement. The stop element may e.g. comprise a pawl or any other suitable components. Thus, although the counteracting member moves to its release position, thereby allowing the stored mechanical energy to be converted into an indexing movement, the stop element will limit the extent of the indexing movement.

The actuator may comprise any suitable type of user control on the medical dispenser, such as a separate button, lever, knob or the like. However, some medical dispensers are provided with an outlet cover which is adapted to open and close the dispenser outlet. Although a separate actuator is conceivable, the outlet cover may suitably be incorporated in the actuator. Thus, either the opening or the closing movement may be used for providing said mechanical energy to be converted to an indexing movement. This is reflected in at least one example embodiment, according to which said actuator comprises an outlet cover adapted to open and close said outlet.

According to at least one example embodiment, said movement of the actuator from the first position towards the second position involves a movement of the outlet cover towards closing the outlet. It should be noted that the second position of the actuator does not necessarily have to coincide with the outlet being completely closed by the outlet cover. The second position may actually be reached before the outlet becomes closed by the outlet cover. Nevertheless, in said embodiment, the direction of movement is such that moving the outlet cover towards closing will build up said mechanical energy, and then on the way to closure (or at complete closure) said built up mechanical energy is released. This may be referred to as "index on closing". As an alternative, it would be conceivable to instead apply "index on opening". That would mean that the outlet cover is moved in the direction from closed towards open in order to build up said mechanical energy (e.g. first position corresponds to completely covered outlet and second position corresponds to at least partly uncovered outlet).

According to at least one example embodiment, the medical dispenser is an inhaler for inhaling a substance. The inhaler may suitably be a dry powder inhaler having discrete doses of inhalable medicament in said compartments. The outlet may be in the form of a mouthpiece or a nasal adaptor.

In the case of the medical dispenser being in the form of an inhaler, the inhalable medicament may contain various active ingredients (drugs and/or bioactive agents) to be inhaled. The active ingredient may be selected from any therapeutic or diagnostic agent. For example, the active ingredient may be an antiallergic, a bronchodilator (e.g. a beta2-adrenoceptor agonist or a muscarinic antagonist), a bronchoconstrictor, a pulmonary lung surfactant, an analgesic, an antibiotic, a mast cell inhibitor, an antihistamine, an anti-inflammatory, an anti-neoplastic, an anaesthetic, an anti-tubercular, an imaging agent, a cardiovascular agent, an enzyme, a steroid, genetic material, a viral vector, an antisense agent, a protein, a peptide, a non-steroidal glucocorticoid Receptor (GR Receptor) agonist, an antioxidant, a chemokine antagonist (e.g. a CCR1 antagonist), a corticosteroid, a CRTh2 antagonist, a DP1 antagonist, an Histone Deacetylase Inducer, an IKK2 inhibitor, a COX inhibitor, a lipoxygenase inhibitor, a leukotriene receptor antagonist, an MPO inhibitor, a p38 inhibitor, a PDE inhibitor, a PPARγ agonist, a protease inhibitor, a statin, a thromboxane antagonist, a vasodilator, an ENAC blocker (Epithelial Sodium-channel blocker) and combinations thereof.

Examples of specific active ingredients that can be incorporated in the inhaler include:
(i) antioxidants:—Allopurinol, Erdosteine, Mannitol, N-acetyl cysteine choline ester, N-acetyl cysteine ethyl ester, N-Acetylcysteine, N-Acetylcysteine amide and Niacin;
(ii) chemokine antagonists:—BX471 ((2R)-1-[[2-[(aminocarbonyl)amino]-4-chlorophenoxy]acetyl]-4-[(4-fluorophenyl)methyl]-2-methylpiperazine monohydrochloride), CCX634, N-{2-[((2S)-3-{[1-(4-chlorobenzyl)piperidin-4-yl]amino}-2-hydroxy-2-methylpropyl)oxy]-4-hydroxyphenyl}acetamide (see WO 2003/051839), and 2-{2-Chloro-5-{[(2S)-3-(5-chloro-1'H,3H-spiro[1-benzofuran-2,4'-piperidin]-1'-yl)-2-hydroxypropyl]oxy}-4-[(methylamino)carbonyl] phenoxy}-2-methylpropanoic acid (see WO 2008/010765), 656933 (N-(2-bromophenyl)-N'-(4-cyano-1H-1,2,3-benzotriazol-7-yl)urea), 766994 (4-({[({[(2R)-4-(3,4-dichlorobenzyl)morpholin-2-yl] methyl}amino)carbonyl]-amino}methyl)benzamide), CCX-282, CCX-915, Cyanovirin N, E-921, INCB-003284, NCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) and Vicriviroc
(iii) Corticosteroids:—Alclometasone dipropionate, Amelometasone, Beclomethasone dipropionate, Budesonide, Butixocort propionate, Ciclesonide, Clobetasol propionate, Desisobutyrylciclesonide, Etiprednol dicloacetate, Fluocinolone acetonide, Fluticasone Furoate, Fluticasone propionate, Loteprednol etabonate (topical) and Mometasone furoate.
(iv) DP1 antagonisits:—L888839 and MK0525;
(v) Histone deacetylase inducers:—ADC4022, Aminophylline, a Methylxanthine or Theophylline;
(vi) IKK2 inhibitors:—2-{[2-(2-Methylamino-pyrimidin-4-yl)-1H-indole-5-carbonyl]-amino}-3-(phenyl-pyridin-2-yl-amino)-propionic acid;
(vii) COX inhibitors:—Celecoxib, Diclofenac sodium, Etodolac, Ibuprofen, Indomethacin, Meloxicam, Nimesulide, OC1768, OC2125, OC2184, OC499, OCD9101, Parecoxib sodium, Piceatannol, Piroxicam, Rofecoxib and Valdecoxib;
(viii) Lipoxygenase inhibitors:—Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 and Zileuton ((±)-1-(1-Benzo[b]thien-2-ylethyl)-1-hydroxyurea);
(ix) Leukotriene receptor antagonists:—Ablukast, Iralukast (CGP 45715A), Montelukast, Montelukast sodium, Ontazolast, Pranlukast, Pranlukast hydrate (mono Na salt), Verlukast (MK-679) and Zafirlukast;
(x) MPO Inhibitors:—Hydroxamic acid derivative (N-(4-chloro-2-methyl-phenyl)-4-phenyl-4-[[(4-propan-2-ylphenyl)sulfonylamino]methyl]piperidine-1-carboxamide), Piceatannol and Resveratrol;
(xi) Beta2-adrenoceptor agonists:—metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol, indacaterol, salmeterol (e.g. as xinafoate), bambuterol (e.g. as hydrochloride), carmoterol, indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino) hexyl]oxy}-butyl)-benzenesulfonamide; 3-(4-{[6-({(2R)-2-hydroxy-2-[4-hydroxy-3-(hydroxy-methyl)phenyl]ethyl}amino)-hexyl]oxy}butyl)benzenesulfonamide; GSK 159797, GSK 159802, GSK 597901, GSK 642444, GSK 678007; and a compound selected from N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide, N-[2-(Diethylamino)ethyl]-N-(2-{[2-(4-hydroxy-2-oxo-2,3-dihydro-1,3-benzothiazol-7-yl)ethyl] amino}ethyl)-3-[2-(3-chlorophenyl)ethoxy]propanamide, 7-[(1R)-2-({2-[(3-{[2-(2-Chlorophenyl)ethyl] amino}propyl)thio]ethyl}amino)-1-hydroxyethyl]-4-hydroxy-1,3-benzothiazol-2(3H)-one, and N-Cyclohexyl-N³-[2-(3-fluorophenyl)ethyl]-N-(2-

{[2-(4-hydroxy-2-oxo-2,3-dihydro-1,3-benzothiazol-7-yl)ethyl]amino}ethyl)-β-alaninamide or a pharmaceutically acceptable salt thereof (e.g. wherein the counter ion is hydrochloride (for example a monohydrochloride or a dihydrochloride), hydrobromide (for example a monohydrobromide or a dihydrobromide), fumarate, methanesulphonate, ethanesulphonate, benzenesulphonate, 2,5-dichlorobenzenesulphonate, p-toluenesulphonate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), D-mandelate, L-mandelate, cinnamate or benzoate.)

(xii) Muscarinic antagonists:—Aclidinium bromide, Glycopyrrolate (such as R,R-, R,S-, S,R-, or S,S-glycopyrronium bromide), Oxitropium bromide, Pirenzepine, telenzepine, Tiotropium bromide, 3(R)-1-phenethyl-3-(9H-xanthene-9-carbonyloxy)-1-azoniabicyclo[2.2.2]octane bromide, (3R)-3-[(2S)-2-cyclopentyl-2-hydroxy-2-thien-2-ylacetoxy]-1-(2-phenoxyethyl)-1-azoniabicyclo[2.2.2]actane bromide, a quaternary salt (such as [2-((R)-Cyclohexyl-hydroxy-phenyl-methyl)-oxazol-5-ylmethyl]-dimethyl-(3-phenoxy-propyl)-ammonium salt, [2-(4-Chloro-benzyloxy)-ethyl]-[2-((R)-cyclohexyl-hydroxy-phenyl-methyl)-oxazol-5-ylmethyl]-dimethyl-ammonium salt and (R)-1-[2-(4-Fluoro-phenyl)-ethyl]-3-((S)-2-phenyl-2-piperidin-1-yl-propionyloxy)-1-azonia-bicyclo[2.2.2]octane salt wherein the counter-ion is, for example, chloride, bromide, sulfate, methanesulfonate, benzenesulfonate (besylate), toluenesulfonate (tosylate), napthalenebissulfonate (napadisylate or hemi-napadisylate), phosphate, acetate, citrate, lactate, tartrate, mesylate, maleate, fumarate or succinate)

(xiii) p38 Inhibitors:—681323, 856553, AMG548 (2-[[(2S)-2-amino-3-phenylpropyl]amino]-3-methyl-5-(2-naphthalenyl)-6-(4-pyridinyl)-4(3H)-pyrimidinone), Array-797, AZD6703, Doramapimod, KC-706, PH 797804, R1503, SC-80036, SCIO469, 6-chloro-5-[[(2S,5R)-4-[(4-fluorophenyl)methyl]-2,5-domethyl-1-piperazinyl]carbonyl]-N,N,1-trimethyl-α-oxo-1H-indole-3-acetamide, VX702 and VX745 (5-(2,6-dichlorophenyl)-2-(phenylthio)-6H-pyrimido[1,6-b]pyridazin-6-one);

(xiv) PDE Inhibitors:—256066, Arofylline (3-(4-chlorophenyl)-3,7-dihydro-1-propyl-1H-Purine-2,6-dione), AWD 12-281 (N-(3,5-dichloro-4-pyridinyl)-1-[(4-fluorophenyl)methyl]-5-hydroxy-α-oxo-1H-indole-3-acetamide), BAY19-8004 (Bayer), CDC-801 (Calgene), Celgene compound ((βR)-β-(3,4-dimethoxyphenyl)-1,3-dihydro-1-oxo-2H-isoindole-2-propanamide), Cilomilast (cis-4-cyano-4-[3-(cyclopentyloxy)-4-methoxyphenyl]-cyclohexanecarboxylic acid), 2-(3,5-dichloro-4-pyridinyl)-1-(7-methoxyspiro[1,3-benzodioxole-2,1'-cyclopentan]-4-yl)ethanone (CAS number 185406-34-2)), (2-(3,4-difluorophenoxy)-5-fluoro-N-[cis-4-[(2-hydroxy-5-methylbenzoyl)amino]cyclohexyl]-)-3-pyridinecarboxamide), (2-(3,4-difluorophenoxy)-5-fluoro-N-[cis-4-[[2-hydroxy-5-(hydroxymethyl)benzoyl]amino]cyclohexyl]-3-pyridinecarboxamide,), CT2820, GPD-1116, Ibudilast, IC 485, KF 31334, KW-4490, Lirimilast ([2-(2,4-dichlorobenzoyl)-6-[(methylsulfonyl)oxy]-3-benzofuranyl])-urea), (N-cyclopropyl-1,4-dihydro-4-oxo-1-[3-(3-pyridinylethynyl)phenyl]-)-1,8-naphthyridine-3-carboxamide), (N-(3,5-dichloro-4-pyridinyl)-4-(difluoromethoxy)-8-[(methylsulfonyl)amino])-1-dibenzofurancarboxamide), ONO6126, ORG 20241 (4-(3,4-dimethoxyphenyl)-N-hydroxy-)-2-thiazolecarboximidamide), PD189659/PD168787 (Parke-Davis), Pentoxifylline (3,7-dihydro-3,7-dimethyl-1-(5-oxohexyl)-)-1H-purine-2,6-dione), compound (5-fluoro-N-[4-[(2-hydroxy-4-methyl-benzoyl)amino]cyclohexyl]-2-(thian-4-yloxy)pyridine-3-carboxamide), Piclamilast (3-(cyclopentyloxy)-N-(3,5-dichloro-4-pyridinyl)-4-methoxy-benzamide),
PLX-369 (WO 2006026754), Roflumilast (3-(cyclopropylmethoxy)-N-(3,5-dichloro-4-pyridinyl)-4-(difluoromethoxy)benzamide), SCH 351591 (N-(3,5-dichloro-1-oxido-4-pyridinyl)-8-methoxy-2-(trifluoromethyl)-5-quinolinecarboxamide), SelCID™ CC-10004 (Calgene), T-440 (Tanabe), Tetomilast (6-[2-(3,4-diethoxyphenyl)-4-thiazolyl]-2-pyridinecarboxylic acid), Tofimilast (9-cyclopentyl-7-ethyl-6,9-dihydro-3-(2-thienyl)-5H-pyrazolo[3,4-c]-1,2,4-triazolo[4,3-a]pyridine), TPI 1100, UCB 101333-3 (N,2-dicyclopropyl-6-(hexahydro-1H-azepin-1-yl)-5-methyl-4-pyrimidinamine), V-11294A (Napp), VM554NM565 (Vernalis), and Zardaverine (6-[4-(difluoromethoxy)-3-methoxyphenyl]-3(2H)-pyridazinone).

(xv) PDE5 Inhibitors:—Gamma-glutamyl[s-(2-iodobenzyl)cysteinyl]glycine, Tadalafil, Vardenafil, sildenafil, 4-phenyl-methylamino-6-chloro-2-(1-imidazolyl)-quinazoline, 4-phenyl-methylamino-6-chloro-2-(3-pyridyl)-quinazoline, 1,3-dimethyl-6-(2-propoxy-5-methanesulphonylamidophenyl)-1,5-dihydropyrazolo[3,4-d]pyrimidin-4-one and 1-cyclopentyl-3-ethyl-6-(3-ethoxy-4-pyridyl)-pyrazolo[3,4-d]pyrimidin-4-one;

(xvi) PPARγ agonists:—Pioglitazone, Pioglitazone hydrochloride, Rosiglitazone Maleate, Rosiglitazone Maleate ((−)-enantiomer, free base), Rosiglitazone maleate/Metformin hydrochloride and Tesaglitizar;

(xvii) Protease Inhibitors:—Alpha1-antitrypsin proteinase Inhibitor, EPI-HNE4, UT-77, ZD-0892, DPC-333, Sch-709156 and Doxycycline;

(xviii) Statins:—Atorvastatin, Lovastatin, Pravastatin, Rosuvastatin and Simvastatin (xix) Thromboxane Antagonists: Ramatroban and Seratrodast;

(xx) Vasodilators:—A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril), Liposomal treprostinil, PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine and Treprostinil sodium;

(xxi) ENACs:—Amiloride, Benzamil, Triamterene, 552-02, PSA14984, PSA25569, PSA23682 and AER002.

The inhaler may contain a combination of two or more active ingredients, for example a combination of two or more of the specific active ingredients listed in (i) to (xxi) herein above.

In one embodiment the inhaler contains an active ingredient selected from mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7- yl)ethylamino]-N-[2-[2-(4-methylphenyl)ethoxy]ethyl]propane-sulphonamide, hydrochloride, indacaterol, aclidinium bromide, N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide or a pharmaceutically acceptable salt thereof (e.g. dihydrobromide); N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate); a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate); or a combination of any two or more thereof.

Specific combinations of active ingredients which may be incorporated in the inhaler include:—
  (a) formoterol (e.g. as fumarate) and budesonide;
  (b) formoterol (e.g. as fumarate) and fluticasone;
  (c) N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide or a pharmaceutically acceptable salt thereof (e.g. dihydrobromide) and a [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate);
  (d) N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide or a pharmaceutically acceptable salt thereof (e.g. dihydrobromide) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate);
  (e) N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate);
N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl] amino}ethyl)-β-alaninamide or a pharmaceutically acceptable salt thereof (e.g. di-D-mandelate) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate).

According to a second aspect of the invention, there is provided an indexing method for a medical dispenser comprising medicament-containing compartments, the method comprising
  continuously building up mechanical energy,
  disrupting the continuous build-up by releasing said mechanical energy, and
  converting said released mechanical energy into an indexing movement of the medicament-containing compartments.

According to a third aspect of the invention, there is provided an indexing method for a medical dispenser comprising medicament-containing compartments and an actuator, the method comprising
  moving said actuator, wherein movement of said actuator sequentially causes mechanical energy to be built up and then released and converted into an indexing movement of the compartments.

It should be understood that the methods of the second and third aspect of the invention, encompass and may be implemented with any embodiments or any features described in connection with the medical dispenser of the first aspect of the invention, as long as those embodiments or features are compatible with the methods of the second and third aspect.

DETAILED DESCRIPTION OF THE DRAWINGS

Figure 8:
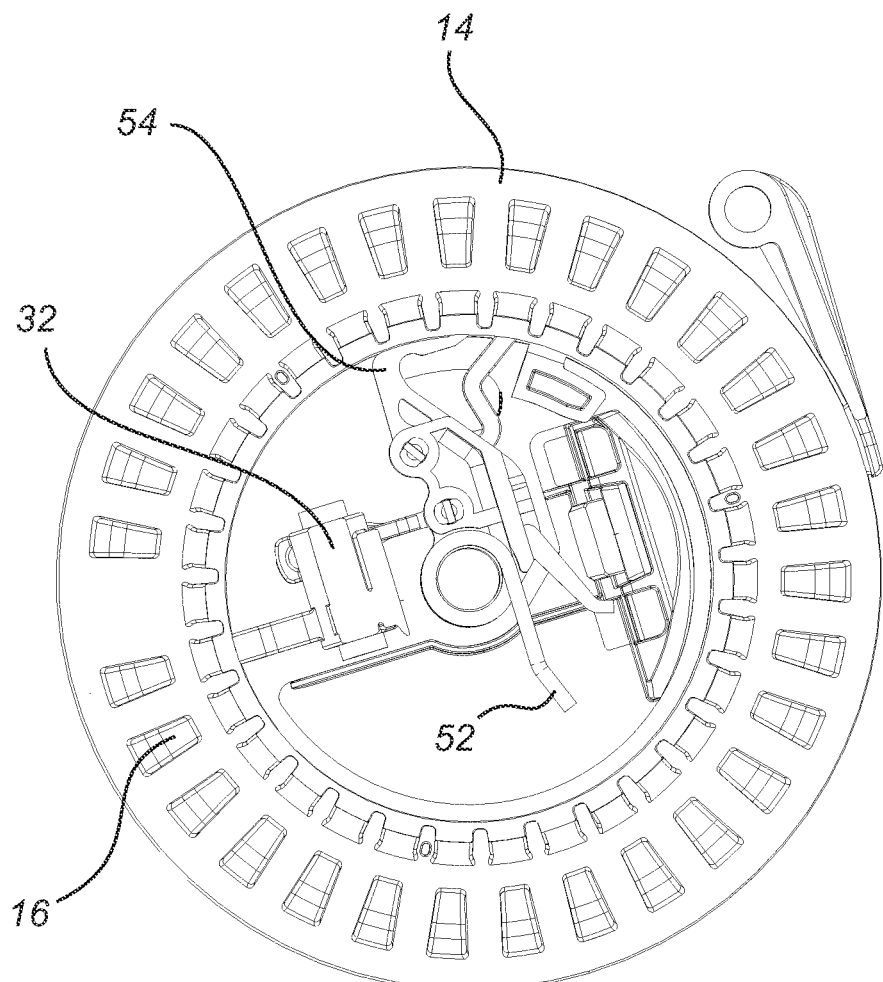

Before providing a detailed description of the various parts of the illustrated medical dispenser, there will first be provided a brief introduction focusing on the inventive concept in relation to an illustrated example embodiment. Accordingly, a medical dispenser in the form of an inhaler 2 comprises an outlet in the form of a mouthpiece 10 (see FIG. 1). A base 14 has a plurality of sealed compartments in the form of sealed cavities 16 which are arranged to be sequentially aligned with and dispensed through the mouthpiece 10. An actuator, herein comprising a mouthpiece cover 12 and an insert 38, is movable between a first position (mouthpiece 10 uncovered) and a second position (mouthpiece 10 covered or almost covered). A closing movement of the mouthpiece cover 12 also causes the insert 38 to move. The insert 38 is connected to an indexing mechanism comprising a torsion spring 52 in which mechanical energy becomes built up as a result of the closing movement of the mouthpiece cover 12. The torsion spring 52 is connected to a drive member 54 for indexing the cavities 16 (see FIGS. 8-10). A counteracting member in the form of a brake 74 is in a counteracting position preventing the indexing movement. The brake 74 comprises a follower 78 which travels in a track 80 of the movable insert 38 (see FIG. 11). When the follower 78 reaches a point of release in the track 80, the brake 74 will move to its release position, which occurs simultaneously with the actuator reaching said second position. The mechanical energy is thereby released and the drive member 54 can perform the indexing movement. In the following, a more detailed description of the medical dispenser will be provided.

Figure 1:
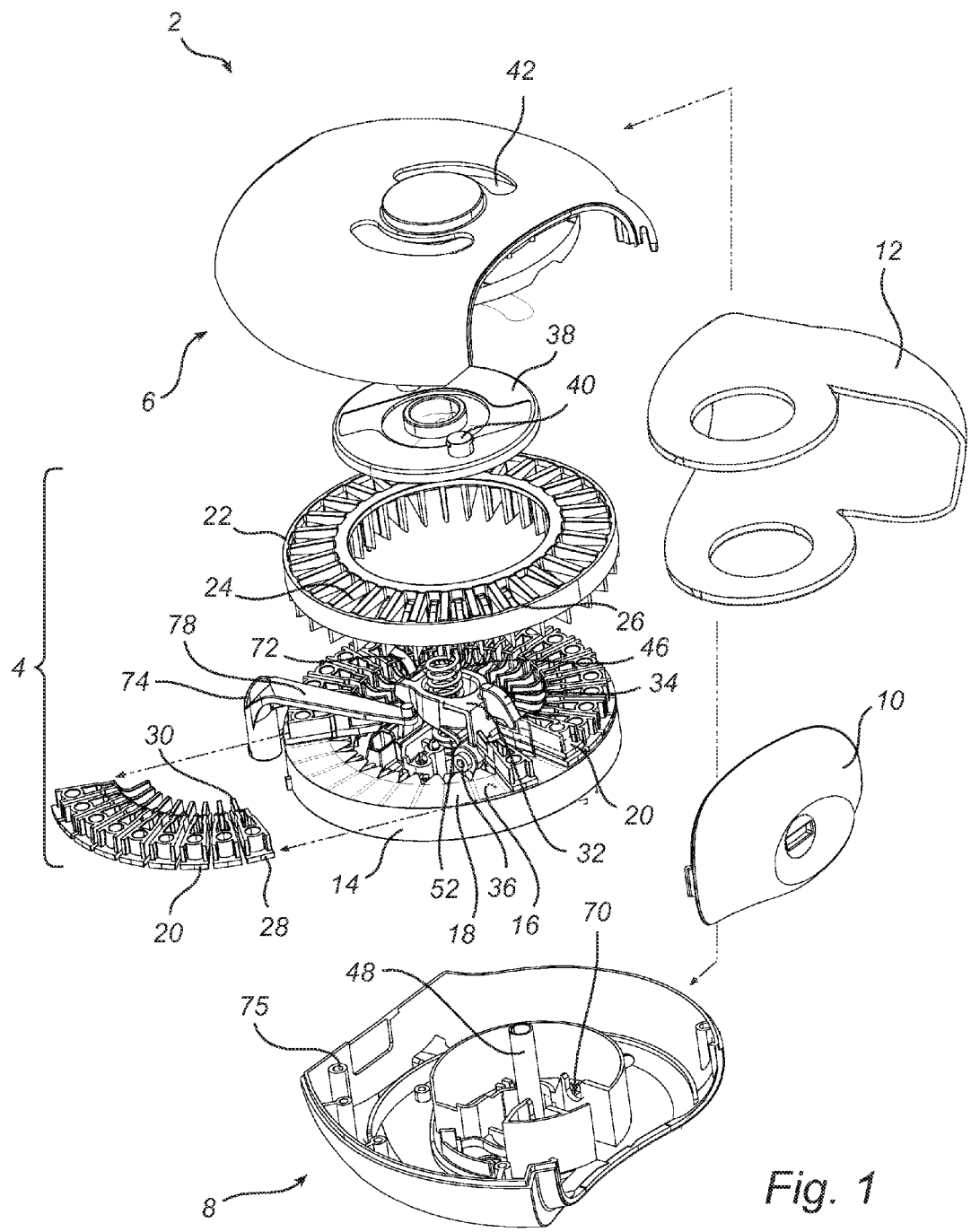
FIG. 1 is an exploded view of a medical dispenser in the form of an inhaler, in accordance with at least one example embodiment of the invention.

FIG. 1 is an exploded view of a medical dispenser in the form of an inhaler 2, in accordance with at least one example embodiment of the invention. The inhaler 2 comprises a dose dispensing assembly 4 having a general disk configuration, an upper housing portion 6, a lower housing portion 8, an outlet herein represented in the form of a mouthpiece 10, and an outlet cover 12. Apart from having the function of alternatingly covering and uncovering the outlet, the outlet cover 12 also has the function of an actuator for building up mechanical energy, as will be explained further on.

The dose dispensing assembly 4 comprises a circular base 14 which has a plurality of sequentially arranged cavities 16 along the circular extension of the base 14. The cavities 16 can be provided with medicament, such as in dry powder form, and are sealed by foil portions 18, thus providing sealed compartments. Thus, the base 14 forms a structure for carrying the compartments. The foil portions 18 are either part of one common foil or provided as separate patches. In the shown example, perforations have been provided to define the foil portions 18 and to facilitate separation from the base 14. Above each cavity 16, a respective associated separating element 20 is attached to the upper side of the foil portion 18. The separating elements 20 are attached by any suitable type of bonding, welding, gluing, etc. to the respective foil portions 18. Upwards movement or lifting of a separating element 20 causes the attached foil portion 18 to become separated from the cavity 16.

A circular guide structure 22 is provided above the separating elements 20. The guide structure 22 comprises a plurality of guide sections 24 divided by vertically extending walls, each guide section 24 being associated with a respective separating element 20. When a separating element 20 is lifted from the cavities-holding base 14, the associated guide section 24 will guide the upwards movement of the separating element 20. Each guide section 24 is provided with a neutralizing element, such as a blade spring 26. After a separating element 20 has been lifted and medicament in the opened cavity 16 has been entrained in the inhalation airflow and the separating element 20 has returned to the base 14, the blade spring 26 will keep the lifted separating element 20 in contact with the base 14 to cover the cavity 16. This will make it difficult for any remaining powder to exit the covered used cavity 16, thus reducing the risk of dose variation which could occur if such remaining powder would be entrained in a following inhalation. It also reduces the risk of remaining powder exiting the cavity 16 and jamming mechanical components in the inhaler or the risk of the separating element creating a rattling noise which would be undesirable for the user. The vertical walls dividing the circular guide structure 22 into guide sections 24 function as lateral flow path defining elements. Thus, an inhalation airflow is prevented from deviating sideways once it reaches the cavity area of the base 14 and will be led to the mouthpiece 10. An alternative would be to have shorter vertical walls, in which case neighbouring separating elements 20 could have the function of lateral flow path defining elements.

Each separating element 20 has a base-covering portion 28 which is in register with a respective cavity 16 in the base. Additionally, each separating element 20 has a centrally projecting portion 30. An opening mechanism comprising a lifter 32 for lifting the separating elements 20 is provided. The lifter 32 is herein represented in the form of a pivotable lever provided with jaws 34 for gripping the centrally projecting portions 30 of the separating elements 20. The lifter 32 has an energized position (FIGS. 2 and 6) in which the jaws 34 are in a lowered position and, after pivoting about a pivot axel 36, an unloaded position (FIGS. 3 and 7) in which the jaws 34 are in a raised position. The lifter 32 with its jaws 34 is only pivotable around the horizontal axel 36 and will thus remain facing the mouthpiece 12 during operation of the inhaler 2.

Returning to FIG. 1, a generally disk-shaped insert 38 is provided under the upper housing portion 6. The upper side of the insert 38 is provided with two pegs 40. The pegs 40 extend upwardly through respective arcuate openings 42 in the upper housing portion 6 and are connected to the outlet cover 12. As the outlet cover 12 is rotated, the pegs 40 will through the arcuate openings 42 transmit the motion to the insert 38 which will also rotate. The underside of the insert 38 is provided with a first force transmitting member, herein illustrated in the form of a cam 44 (see FIG. 4), which will convert the rotating motion to a linear force affecting the jaws 34 of the lifter 32 in order to return the lifter 32 from its unloaded position to its energized position. As the cam 44 comes into contact with the jaws 34 of the lifter 32 (see FIG. 5), the lifter 32 will be moved radially towards the separating element 20 and will rotate around its pivot axel 36. Also, the jaws 34 will drop down to the primed or energized position of the lifter 32 (see FIG. 2). The lowering of the jaws 34 will be against the force of a coil spring 46 which is biased to raise the jaws 34 to the unloaded position. The coil spring 46 is wound around a post 48 projecting upwardly from the lower housing portion 8.

Figure 4:
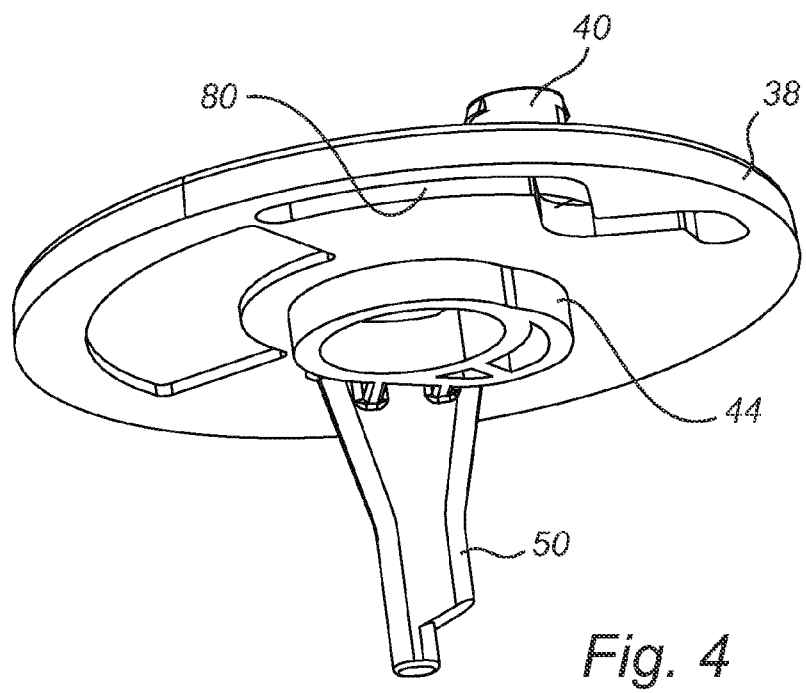
FIGS. 4 to 8 and 11 illustrate various details of the inhaler, including details related to indexing.
Figure 6:
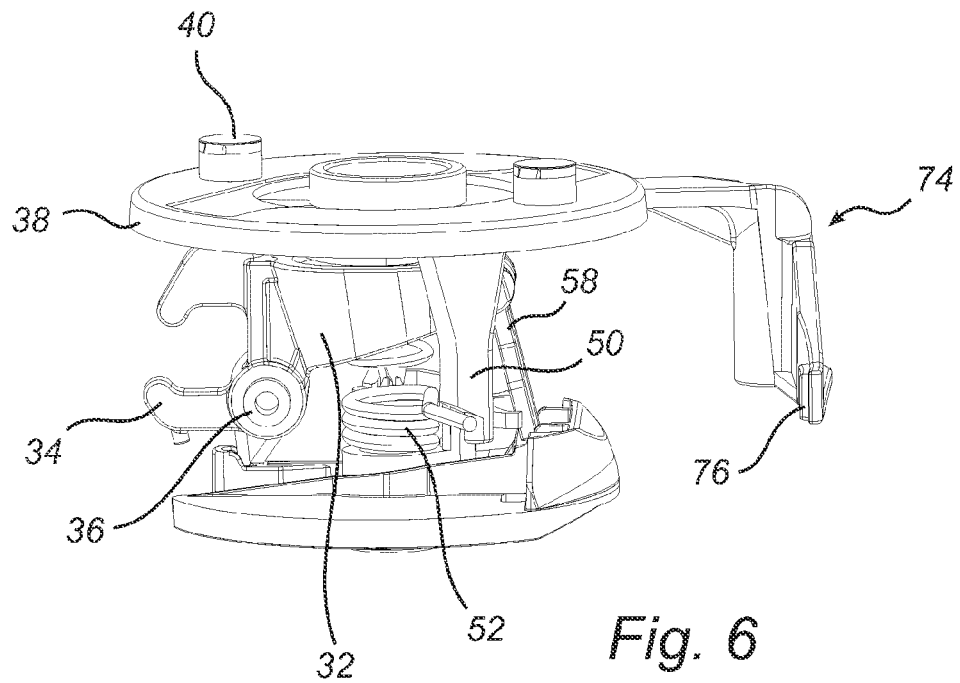
Figure 7:
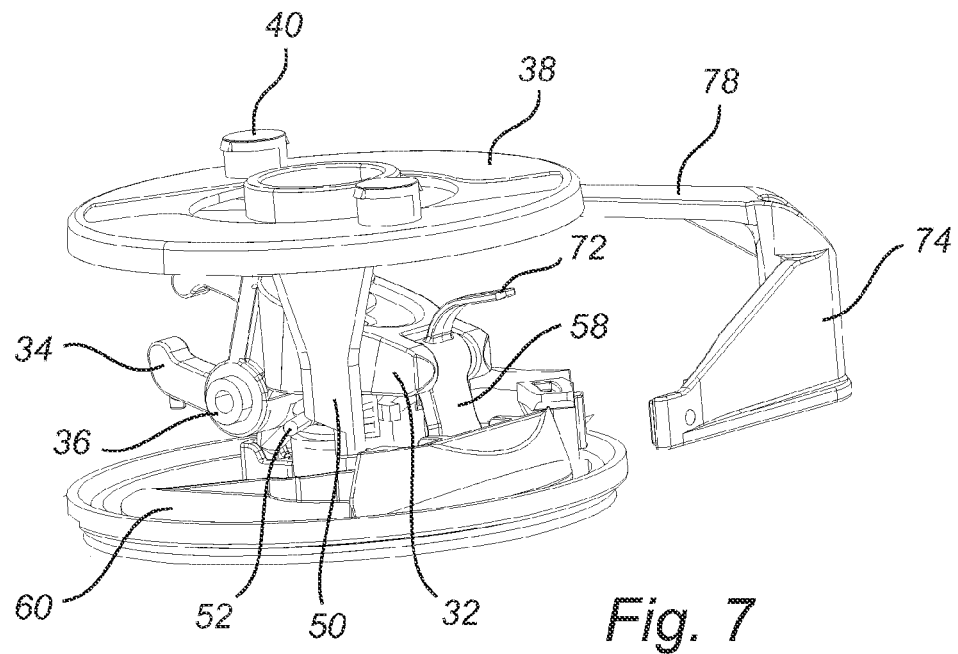

As illustrated in FIGS. 4, 6 and 7, the underside of the insert 38 is also provided with a projecting second force transmitting member 50 which is configured and adapted to engage an end of a torsion spring 52 located under the coil spring 46 and around the same post 48. The torsion spring 52 is connected to a drive member 54 for rotatingly advancing the cavities 16 by one increment at a time, so as to each time bring an unopened cavity in alignment with the mouthpiece 10. The drive member is best seen in FIGS. 8, 9, 10 and 11.

Figure 2:
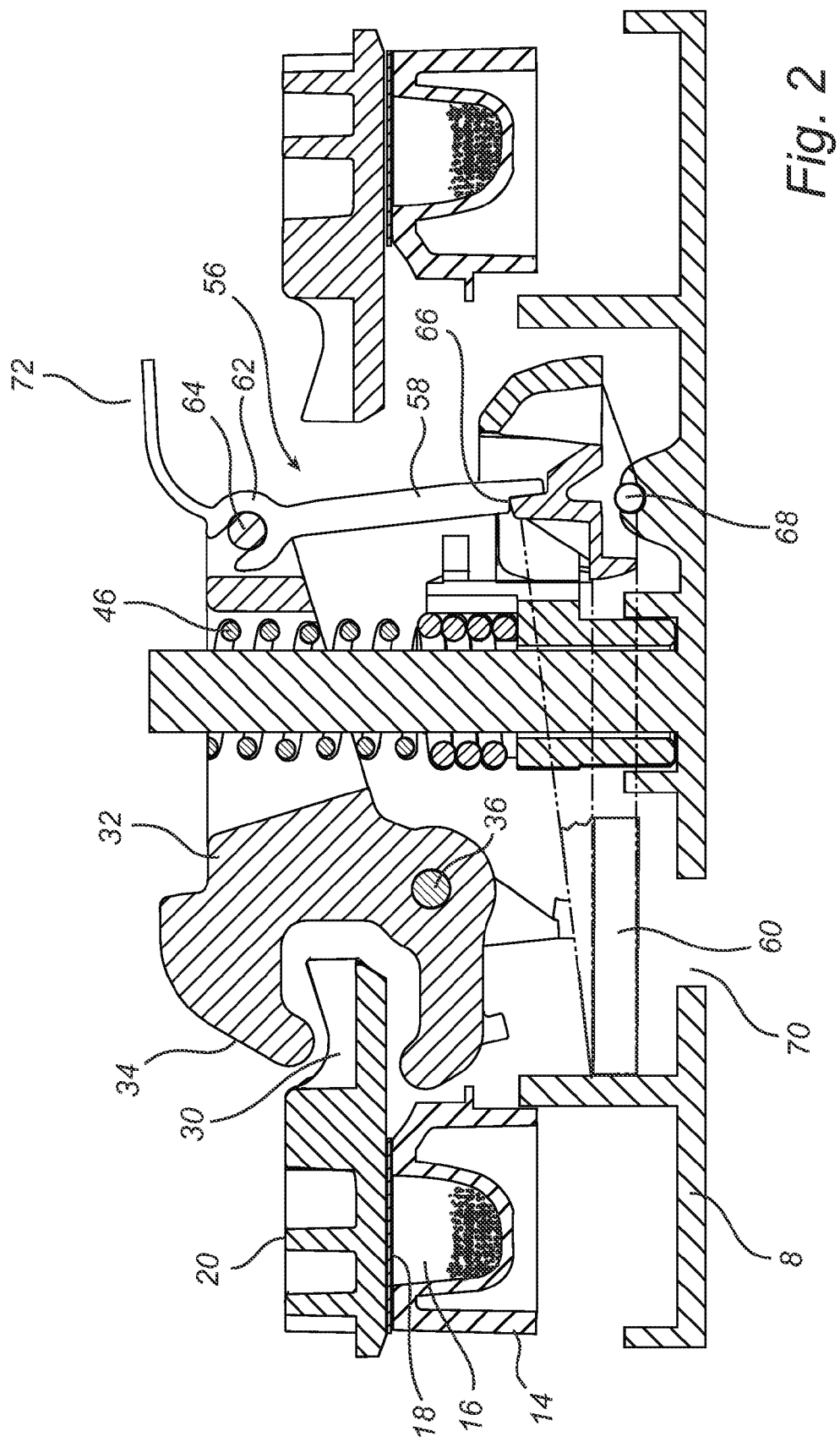
FIG. 2 is a cross-sectional view of selected details of the inhaler.

A latch 56 is provided to keep the lifter in the energized position, which is clearer from FIG. 2. The latch 56 comprises a first element in the form of an elongated prop 58 and a second element in the form of a flap 60. The elongated prop 58 has a first end portion 62 which is pivotable around a first horizontal axle 64 near that end of the lifter 32 which is located distally to the mouthpiece 10 (the jaws 34 being located proximally to the mouthpiece 10). The elongated prop 58 has a second end portion 66 adapted to be supported by the flap 60. The flap 60 is pivotable around a second horizontal axle 68. The flap covers a number of air inlets 70 (FIGS. 1-3) provided in the lower housing portion 8. Air is allowed to enter the inhaler 2 through said air inlets 70 when the user inhales through the mouthpiece 10 (outlet).

FIG. 2 is a cross-sectional view of selected details of the inhaler, wherein the inhaler is in a primed state, i.e. the lifter 32 is latched in an energized position. Thus, the jaws 34 of the lifter 32 have been lowered against the force of the coil spring 46 and now enclose the centrally projecting portion 30 of a separating element 20 aligned with the mouthpiece. The second end portion 66 of the elongated prop 58 is supported by a mating portion of the flap 60. The latch 56 comprising the prop 58 and the flap 60 is now in its first position, in which it latches the lifter 32 in the energized position. The latch 56 is biased towards its first position. More specifically, in this exemplified embodiment, the interface or contact point between the second end portion 66 of the elongated prop 58 and the flap 60 is located on the same side of the second horizontal axle 68 as is the portion of the flap 60 covering the air inlets 70 (in FIG. 2, the contact point between the elongated prop 58 and the flap is located left of the second horizontal axle 68). Thus, the centre of mass and the force on the flap 60 provided by the elongated prop 58 will be located left (in FIG. 2) of the pivot point provided by the second horizontal axle 68, thereby keeping the flap 60 in the illustrated lowered position. As long as the flap 60 remains still, the prop 58 is also prevented from moving, thereby keeping the lifter 32 latched in its energized position. The force exerted on the flap 60 is suitably adjusted to correspond to an airflow threshold which is exceedable by a user's inhalation. A position-keeping element 72 is provided at the first end portion 62 of the prop 58. From above, the position-keeping element 72 will be in contact with the disk-shaped insert 38 (FIG. 1). That contact will ensure that the prop 58 does not accidentally pivot around the first horizontal axle 64 in case the user should turn the inhaler in a different orientation (e.g. upside down) when closing the outlet cover 12. Thus, the flap 60 and prop 58 will be able to latch the actuator 32 even if a user holds the inhaler upside down when closing the outlet cover 12.

In at least one other embodiment, the illustrated position-keeping element 72 could rather function as a biasing spring element 72. In such an embodiment, the biasing spring element 72, would not just be in contact with the disk-shaped insert 38 (FIG. 1), but would actually be pressed downwardly by the disk-shaped insert 38. This force exerted on the biasing spring element 72 would have a levering effect about the first axle 64, urging the second end portion 66 of the prop 58 in a direction towards the jaws 34 and the mouthpiece (clockwise rotation in FIG. 2). This urging of the second end portion 66, which is in contact with a mating portion of the flap 60, would keep the flap 60 biased in the illustrated substantially horizontal lowered position. The biasing force transmitted from the biasing spring element 72 to the flap 60 would suitably be adjusted to correspond to an airflow threshold which is exceedable by a user's inhalation.

In another embodiment (not shown in the Figures), the element 72 could be replaced by a spring located on the insert 38. This could be a steel spring, for example, bearing on a small projection at the top of the prop 58 in order to bias it in essentially the same way as the element 72.

Figure 3:
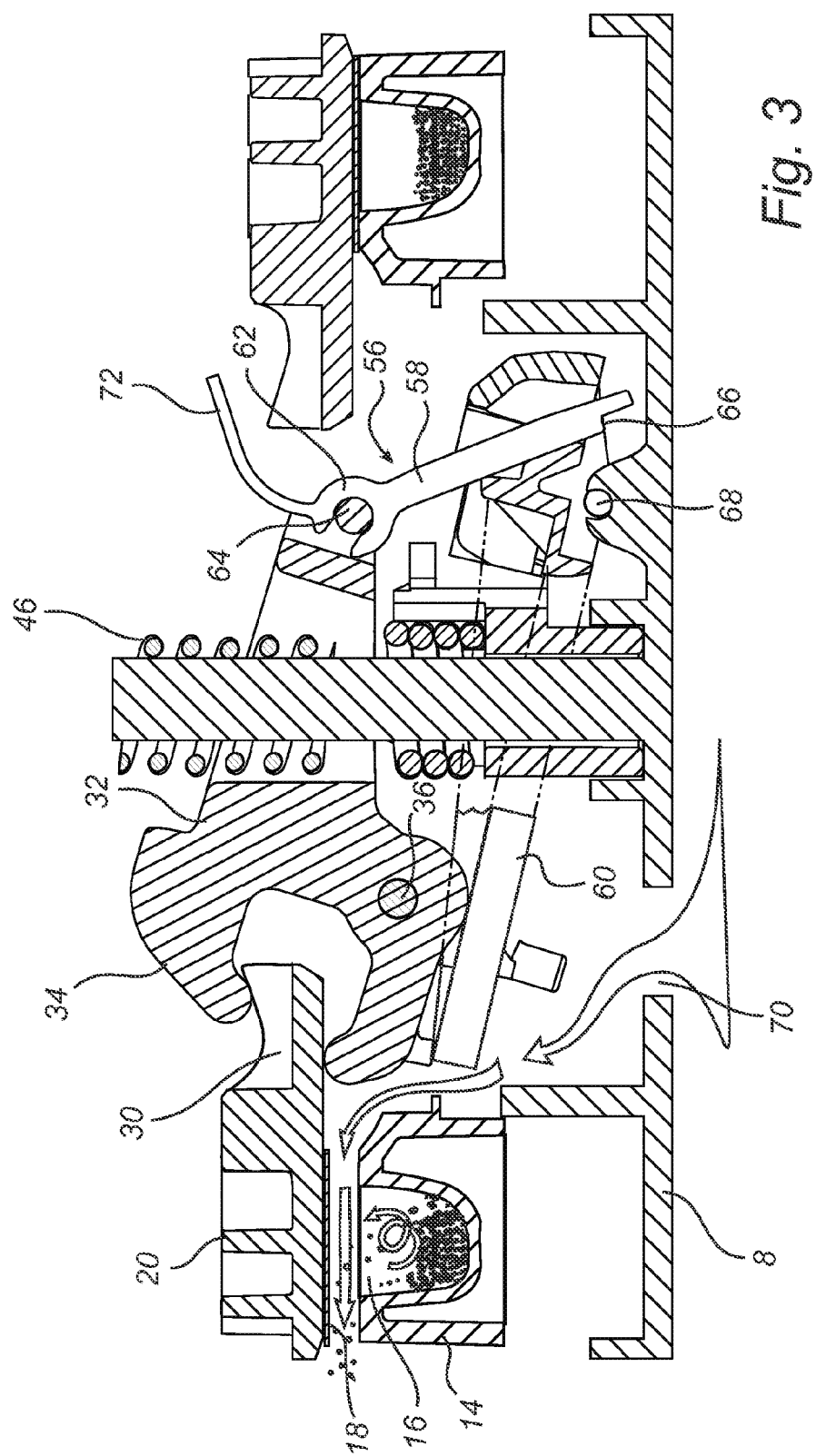
FIG. 3 illustrates, at the time of dispensing medicament from the inhaler, a cross-sectional view of selected details of the inhaler.

Thus, in order to administer a dose, the user inhales creating a sufficient airflow to raise the flap 60 against the biasing force. This is illustrated in FIG. 3. As the flap 60 is raised by the airflow and pivoted around the second axle 68 (clockwise in FIG. 3), the mating portion of the flap 60, being on the other side of the axle is lowered, whereby the second end portion 66 of the prop 58 loses its support. This will cause the prop 58 to pivot around the first axle 64 (anticlockwise in FIG. 3) and to "roll" off the mating portion of the flap 60. The latch 56 is now in its second position, in which it allows the lifter 32 to move to said unloaded position. Thus, the stored energy of the coil spring 46 will cause the now released lifter 32 to move. The lifter 32 will pivot around its axle 36 and the jaws 34 will be raised, whereby the engaged separating element 20 is lifted from the base 14. The foil portion 18 remains attached to the separating element 20, thus opening the medicament-containing cavity 16. FIG. 1 illustrates with dashed lines a separating element 20 being raised by the jaws 34 of the lifter 32.

It is realized that the design of the exemplified inhaler 2 provides for use of a phenomenon denoted as shear driven cavity principle during deaggregation of the powder in the cavity 16 and emptying of the powder therefrom. The shear driven cavity is a model for flow in a cavity where the upper boundary moves in a desired flow direction, and thus causes a rotation in the cavity. FIG. 2 illustrates a medicament powder-containing cavity 16 having a suitable headspace above the powder. In FIG. 3, the inhalation airflow passes by said headspace along a flat surface region, said flat surface region comprising the opening into the powder-containing cavity 16. The horizontal passing of the inhalation airflow leads to a build-up of an eddy air stream in the cavity 16 which causes powder to be deaggregated and emptied from the cavity 16. The cavity 16 is generally brick-shaped and the cavity opening has a rim where the sides of the cavity transcend into the flow passage flat surface region. Accordingly, the airflow, when passing the cavity in the flow passage, preferably flows in parallel with a plane coinciding with the rim of the cavity opening in the flow passage.

While the flap 60 may return to the lowered position after a dose is dispensed, the jaws 34 of the lifter 32 will remain in the unloaded position (see e.g. FIG. 7) until the user primes the inhaler for the next dose.

Although the priming of the inhaler 2 may be coupled to either the opening or closing of the outlet cover 12, in this example embodiment, it is assumed that closing of the outlet cover 12 primes the inhaler 2. Thus, when the user has inhaled a dose (FIGS. 3 and 7), he/she will close the outlet cover 12 to cover the mouthpiece 10 (FIG. 1). Although, the outlet cover 12 may be designed to form various travel paths, such as linear or stepwise paths, in this example embodiment the outlet cover 12 is rotated to cover the mouthpiece 10. During such closing of the outlet cover 12, the connected insert 38 with its force transmitting projecting member 50 and cam 44 will cause the jaws 34 of the lifter 32 to be lowered against the force of the coil spring 46 (FIG. 5) and the base 14 to be rotated, thus presenting an unopened next cavity 16 to the jaws 34. The insert 38 will also press the position-keeping element 72 of the prop 58, causing the latch 56 to return to its first position, whereby the lifter 32 is prevented from lifting its jaws 34. After that, when the user opens the outlet cover 12 in order to take another dose, the insert 38 will rotate the other way without affecting the latched and energized lifter 32. The inhaler 2 is now primed (triggered) and ready to be fired when the user breaths in through the mouthpiece 10, thereby enabling breath-triggered lifting of a foil portion 18 from a cavity 16.

In order to reduce the risk of latching the lifter 32 in the energized position without having aligned an unopened cavity 16, the latch 56 is prevented from returning to the first latching position before the next cavity is aligned with the mouthpiece 10. Also in order to reduce the risk of overindexing, i.e. passing an unopened cavity 16 past the mouthpiece 10 without opening the cavity 16, an indexing mechanism for sequentially aligning the cavities with the mouthpiece 10 is provided, wherein the indexing mechanism is adapted to align the next cavity 16 with the mouthpiece 10 after the lifter 32 has been moved from the unloaded position to the energized position.

Thus, in the illustrated example embodiment, after a dose has been dispensed, the user closes the outlet cover 12. As has been described above, the rotation of the outlet cover 12 causes the generally disk-shaped insert 38 to rotate. Through the rotation of the insert 38, the provided cam 44 will urge the lifter 32 (see FIG. 5) to move to its energized position. Thus, the jaws 34 of the lifter 32 will move from the raised unloaded position illustrated in FIGS. 3 and 7 to the lowered energized position illustrated in FIGS. 2 and 6.

Substantially simultaneously with the cam 44 urging the lifter 32, through the rotation of the insert 38, the projecting second force transmitting member 50 will urge the indexing mechanism to advance the next cavity 16 to be aligned with the mouthpiece 10. More particularly, as illustrated in FIG. 6, the projecting member 50 will build up mechanical energy in the torsion spring 52 which is connected to the drive member 54 (see FIG. 8). The energized torsion spring 52 will urge the connected drive member 54 to rotate around the central axis provided by the post 48 (see FIG. 1) in order to engage the base 14 and to thereby cause the base 14 to rotate so as to bring the next cavity 16 aligned with the mouthpiece.

However, the force on the drive member 54 provided by the projecting member 50 via the torsion spring 52 is temporarily counteracted, at least until the lifter 32 has reached its energized position (and the actuator has reached its second position). If the jaws 34 of the lifter 32 would not be lowered before indexing, the separating element 20 next in turn would risk hitting the jaws 34 during the indexing.

Figure 5:
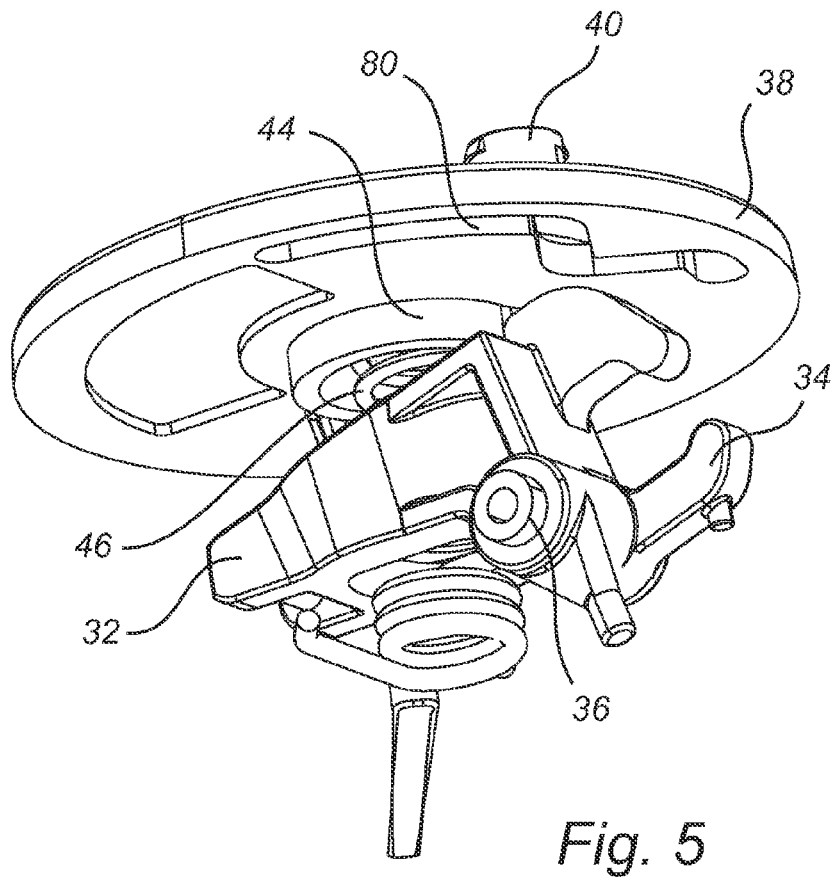
Figure 10:
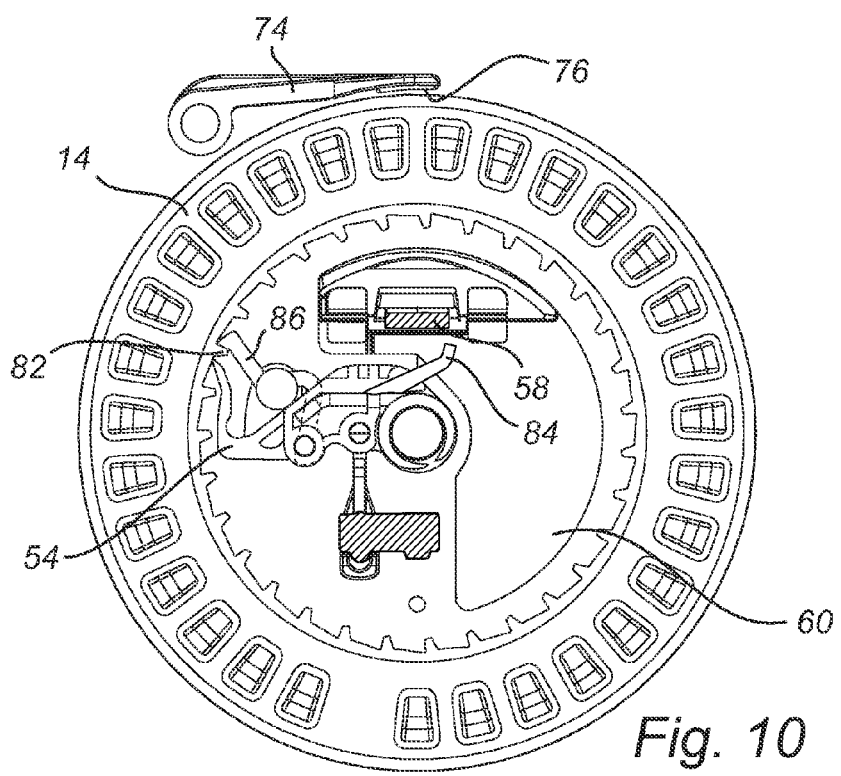
FIG. 10 is a cross-sectional view of selected details of the inhaler after indexing.
Figure 11:
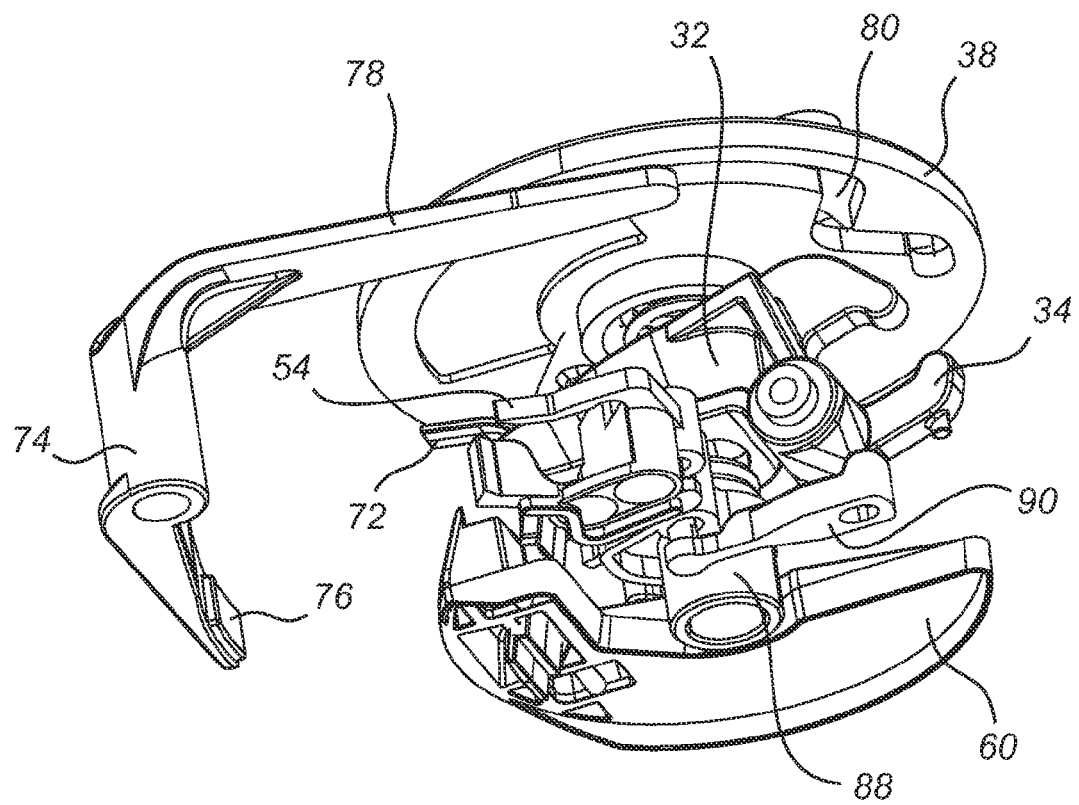

The counteracting member comprises a brake 74 adapted to prevent the compartments from moving. The brake 74 is attached to a lateral post 75 projecting from the lower housing portion 8 (see FIG. 1). The brake comprises a brake pad 76 which is pressed against the outer enveloping surface of the base 14 (see FIG. 9), thereby preventing the base 14 from rotating. The counteracting member also comprises a follower 78 (see FIGS. 1 and 11) which is connected to the brake 74 and which travels in a track 80 provided in the underside of the generally disk-shaped insert 38. The track 80 is best seen in FIGS. 4, 5 and 11, wherein FIG. 11 demonstrates how the follower 78 travels in the track 80. Thus, as the follower 78 travels in the track 80, it will follow an irregular path and when it reaches a point of release (coordinated with the actuator reaching its second position), the connected brake 74 lets go of the base 14 (FIG. 10). Now, the mechanical energy is released and the drive member 54 can perform the indexing movement. Thus, the base 14 will be rotated by the drive member 54 which is urged by the torsion spring 52 as previously explained. Thus, the above exemplified mechanical sequencing assembly provides for alternate energizing of the opening mechanism (herein exemplified as the jawed lifter 32) and indexing of the compartments (herein exemplified as sealed cavities 16 in a base 14).

Figure 9:
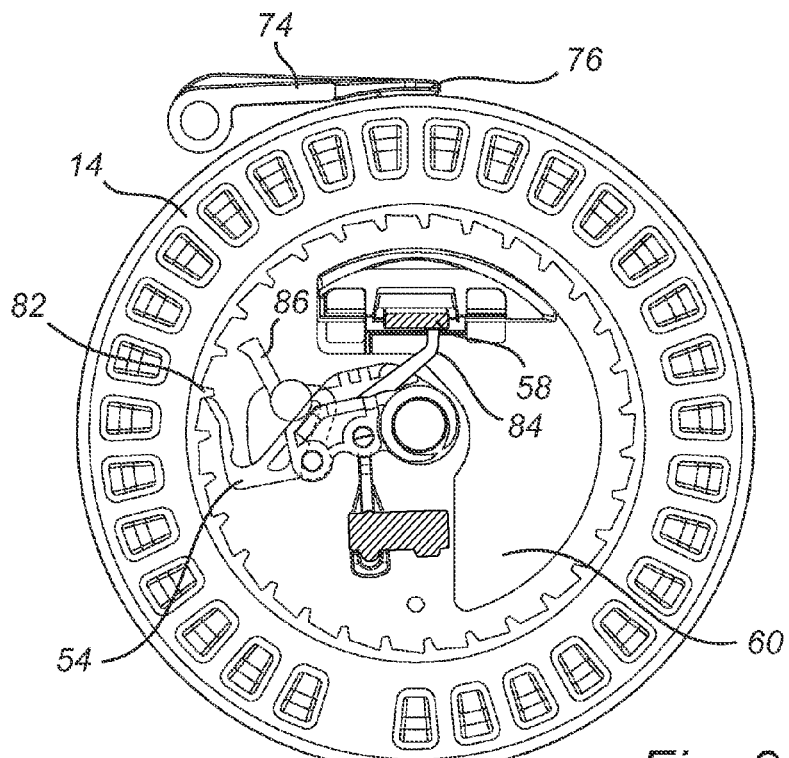
FIG. 9 is a cross-sectional view of selected details of the inhaler before indexing.

As illustrated in FIG. 9, before the brake 74 is released an end portion of the drive member 54 engages one of a plurality of teeth 82 in the base 14. An arm-shaped catch 84 is connected to the drive member 54 and may even be formed in one piece with the drive member 54. The catch 84 is in a preventing position, in which it prevents the first element (prop 58) of the latch 56 from becoming supported by the second element (flap 60) of the latch 56. Thus, in this state of the inhaler, the lifter cannot become latched in the energized position. Thus, the risk of re-firing from the same cavity 16 is reduced.

As the brake 74 is released, the drive member 54 will via the engaged tooth 82 rotate the base 14 one cavity-step. FIGS. 9 and 10 also illustrate a stop element in the form of a pawl 86 being pivotally mounted at a pivot point of the drive member (indicated with dashed lines). In FIG. 9, the pawl 86 is retracted, while in FIG. 10 the pawl 86 has been advanced to engage with a tooth 82, herein illustrated as engaged with the opposite side of the same tooth 82 that is pushed by the drive member 54. The pawl 86 prevents the drive member 54 from over-rotating the base 14, ensuring that the inhaler is indexed only one cavity-step at a time.

The drive member 54 and the catch 84 are connected to a common barrel 88 (best seen in FIG. 11) which swivels around the central post 48 (FIG. 1) projecting upwardly from the lower housing portion 8. As the drive member 54 rotates the base 14 the catch 84 will be removed from the preventing position, as illustrated in FIG. 10, thereby allowing the prop 58 to become supported by the flap 60 and latch the energized lifter. The inhaler is now primed.

As previously described, in particular in connection with FIGS. 2 and 3, when the user opens the outlet cover 12 and inhales through the mouthpiece 10, the flap 60 is raised so that the prop 58 comes off the flap 60, thereby unlatching the lifter 32. The lifter 32 being energized by the coil spring 46 will be raised so that the jaws 34 of the lifter 32 remove the separating element 20 and the foil portion 18 from the cavity 16 presently aligned with the mouthpiece 10. As can be seen in FIG. 11, a movable pulling arm 90 connects the drive member 54 with the lifter 32. As the lifter 32 and the jaws 34 are raised, the pulling arm 90 follows that motion whereby at the other end of the pulling arm 90, the drive member 54 will be pulled from the primed state shown in FIG. 10 to the fired state shown in FIG. 9. The catch 84 will consequently be moved back to its preventing position shown in FIG. 9. Next, when the user closes the outlet cover 12, the inhaler will once again become primed.

If the user, for some reason, does not close the outlet cover 12 enough, the follower 78 travelling in the track 80 will not reach its point of release, and consequently the brake 74 will not be released. This in turn means that there will be no indexing. Furthermore, although the lifter 32 is in its energized position, it will not become latched, as latching can only occur in connection with indexing, as explained above. Thus, if the user then opens the outlet cover 12, which has not been fully closed, the lifter 32 will simply move back to its unloaded position.

The herein discussed indexing mechanism, enables rotation of the base 14 to be limited to one direction. Thus, un-indexing may be prevented from occurring. This may be advantageous in connection with other types of opening mechanisms or separating elements.

It should be noted that in this application terms such as "upper", "lower", "above", "below" have been used for explanatory purposes to describe the internal relationship between elements of the inhaler, regardless of how the inhaler is oriented in the surrounding environment. For instance, in the exemplified embodiment in the drawings, the cavities 16 are regarded as being placed "below" the foil portions 18, while the separating elements 20 are regarded as being placed "above" the foil portions 18, regardless of how the inhaler 2 as a whole is held or turned by the user. Similarly, "horizontal" means a direction located in the plane of the foil portions 18 or any plane parallel to the plane of the foil portions 18, and "vertical" means any direction perpendicular to such planes. Thus, a vertical line may intersect the cavities 16, the foil portion 18 and the separating elements 20.

Most components of the inhaler 2, such as outlet cover 12, the base 14, the separating elements 20, the lifter 32, the insert 38, the drive member 54 and the latch 56 are suitably made of a plastic material, such as a polymer, however, other materials, such as metal or ceramic are conceivable alternatives.

The inhaler 2 may suitably comprise a structure that provides a moisture protection, such as e.g. a moisture absorbent sink as described in WO2006/000758, or any other appropriate alternative for including desiccant material.

It should be noted that although the drawings have been illustrated in connection with a dry powder inhaler having a disk with sealed cavities, the inventive concept encompasses and may be applied to other types of inhalers as well. Thus, the building up of mechanical energy and its release and conversion into an indexing movement may be applied to devices with strips carrying compartments, or blister packs, or any other form of dose carrying structure which can be indexed. Consequently, the inventive concept may be used with other types of opening mechanisms, such as mechanisms which pierce or punch through the compartments to enable access to the medicament. Furthermore, the inventive concept is not limited to inhalers, but includes other types of medical dispensers, such as packages containing tablets, pills or capsules, which are accessible via an outlet.

In a further embodiment (not shown in the figures), the cover 12 could be replaced by a cover which extends over the majority of the housing. The cover would be rotatable with respect to the housing between an open configuration in which the mouthpiece is exposed and a closed configuration in which the mouthpiece as well as the majority of the housing is enclosed in the cover. The cover could have, formed on its internal surface, the cam surfaces 44, 50, 80 which are in previous embodiments associated with the insert 38. An aperture in the housing would be provided through which some or all of the cam surfaces, e.g. the cam surface 50, could project in order to engage with the corresponding parts of the mechanism inside the housing (e.g. indexing spring 52).

The invention claimed is:

1. A medical dispenser, comprising:
an outlet;
a plurality of sealed compartments configured to contain medicament to be sequentially aligned with and dispensed through said outlet;
an actuator movable between a first position and a second position, wherein movement of the actuator from the first position towards the second position causes mechanical energy to be built up, and wherein the arrival of the actuator at the second position causes the built-up mechanical energy to be released and converted into an indexing movement of the compartments;
a track configured to move with the actuator;
an indexing mechanism for sequentially aligning the compartments with the outlet, wherein the indexing mechanism is operatively connected to the actuator, wherein said mechanical energy is built up in the indexing mechanism;
a counteracting member having a counteracting position, in which the counteracting member temporarily prevents said mechanical energy from being released, and a release position, in which the mechanical energy is released whereby the indexing mechanism is allowed to advance the compartments, wherein the counteracting member is operatively connected to the actuator such that the counteracting member reaches said release position when the actuator reaches said second position, wherein the counteracting member includes a brake configured to prevent the compartments from moving and a follower connected to the brake and configured to travel along said track in response to the movement of the actuator, wherein, when the follower reaches a point of release, the connected brake is released.

2. The medical dispenser of claim 1, wherein, in said counteracting position, the counteracting member is in a fixating contact with one or more compartments or with a structure carrying the compartments.

3. The medical dispenser of claim 1, further comprising a rotatable disk holding said compartments, wherein, in said counteracting position, the counteracting member engages the disk to prevent it from rotating.

4. The medical dispenser of claim 1, further comprising a stop element which, during said indexing movement, is configured to engage with the compartments or a structure carrying the compartments in order to limit said movement.

5. The medical dispenser of claim 1, wherein said indexing mechanism comprises a spring in which said mechanical energy is built up.

6. The medical dispenser of claim 5, wherein said indexing mechanism comprises a drive member which is engagable with the compartments or a structure carrying the compartments, the drive member being connected to the spring so that when the counteracting member reaches said release position, the accumulated mechanical energy in the spring is transmitted via the drive member to the compartments.

7. The medical dispenser of claim 1, wherein said actuator comprises an outlet cover configured to open and close said outlet.

8. The medical dispenser of claim 7, wherein said movement of the actuator from the first position towards the second position involves a movement of the outlet cover towards closing the outlet.

9. The medical dispenser of claim 1, wherein the medical dispenser is an inhaler.

10. The medical dispenser of claim 9, wherein the medicament comprises an active ingredient including one or more of mometasone; ipratropium bromide; tiotropium and salts thereof; salemeterol; fluticasone propionate; beclomethasone dipropionate; reproterol; clenbuterol, rofleponide and salts; nedocromil; sodium cromoglycate; flunisolide; budesonide; formoterol fumarate dihydrate; terbutaline; terbutaline sulphate; salbutamol base and sulphate; fenoterol; 3-[2-(4-Hydroxy-2-oxo-3H-1,3-benzothiazol-7-yl)ethylamino]-N-[2-[2-(4-methylphenyl)ethoxy]ethyl]propane-sulphonamide; hydrochloride; indacaterol; aclidinium bromide; N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g., dihydrobromide); N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g., di-D-mandelate); a [2-(4-Chloro-benzyloxy)-ethyl]-[2-((R)-cyclohexyl-hydroxy-phenyl-methyl)-oxazol-5-ylmethyl]-dimethyl-ammonium salt (e.g., hemi-naphthalene-1,5-disulfonate); and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g., bromide or toluenesulfonate).

11. A medical dispenser, comprising:
an outlet;
a plurality of compartments;
an actuator, wherein movement of the actuator from a first position towards a second position causes mechanical energy to be built up, and wherein the arrival of the actuator at the second position causes the built-up mechanical energy to be released and converted into an indexing movement of the compartments;
a track configured to move with the actuator;
an indexing mechanism for sequentially aligning the compartments with the outlet; and
a counteracting member having a counteracting position, in which the counteracting member prevents the release of the mechanical energy, and a release position, in which the mechanical energy is released whereby the indexing mechanism is allowed to advance the compartments, wherein the counteracting member includes a brake configured to prevent the compartments from moving and a follower connected to the brake and configured to travel along said track in response to the movement of the actuator, wherein, when the follower reaches a point of release, the connected brake is released.

12. The medical dispenser of claim 11, wherein said indexing mechanism comprises a spring in which said mechanical energy is built up.

13. The medical dispenser of claim 11, wherein, in said counteracting position, the counteracting member is in a fixating contact with one or more compartments or with a structure carrying the compartments.

14. The medical dispenser of claim 11, further comprising a rotatable disk holding said compartments, wherein, in said counteracting position, the counteracting member engages the disk to prevent it from rotating.

15. The medical dispenser of claim 11, further comprising a stop element which, during said indexing movement, is configured to engage with the compartments or a structure carrying the compartments in order to limit said movement.

* * * * *